(12) United States Patent
Kobata et al.

(10) Patent No.: US 6,197,985 B1
(45) Date of Patent: Mar. 6, 2001

(54) SOLID ALUMINOXANE FOR CATALYST CARRIER, PROCESS FOR PREPARING THE SAME, AND USES THEREOF

(75) Inventors: Atsuo Kobata; Kazuhito Gotoh; Shigeru Isayama; Tetsuhiro Matsumoto, all of Waki-cho (JP)

(73) Assignee: Mitsui Chemicals INC, Tokyo (JP)

( * ) Notice: Subject to any disclaimer, the term of this patent is extended or adjusted under 35 U.S.C. 154(b) by 0 days.

(21) Appl. No.: 09/144,978

(22) Filed: Sep. 1, 1998

(30) Foreign Application Priority Data

| Sep. 3, 1997 | (JP) | 9-237922 |
| Jul. 24, 1998 | (JP) | 10-209806 |
| Jul. 24, 1998 | (JP) | 10-209807 |
| Jul. 24, 1998 | (JP) | 10-209808 |

(51) Int. Cl.[7] .............. C07F 5/06; C07F 17/00; B01J 31/00
(52) U.S. Cl. ............ 556/175; 556/178; 556/182; 502/103; 502/109; 502/117; 526/160; 526/943
(58) Field of Search .................... 556/175, 178, 556/182; 502/103, 117, 109; 526/160, 943

(56) References Cited

U.S. PATENT DOCUMENTS 4,923,833  5/1990  Kioka et al. .............. 502/9
4,952,540 * 8/1990  Kioka et al. .............. 502/9

FOREIGN PATENT DOCUMENTS

| 0279586 | 8/1988 | (EP) . |
| 0360492 | 3/1990 | (EP) . |
| 0612753 | 8/1994 | (EP) . |

OTHER PUBLICATIONS

Chemical Abstracts, vol. 115, No. 22, Dec. 2, 1991, Columbus, Ohio, Abstract No. 232981, "Gas phase polymerization with a solid catalyst. . . ".

* cited by examiner

Primary Examiner—Porfirio Nazario-Gonzalez

(57) ABSTRACT

A low-bulk density solid aluminoxane has an average particle diameter of 210 to 10,000 μm and a bulk density of from 0.01 to 1.0 g/cc. Representative solid aluminoxanes may be prepared from polymethylaluminoxane or mixed alkyl group aluminoxanes. The solid aluminoxanes are useful as catalyst carriers. When used to support a metallocene, the combination may be used, for example, as catalyst for olefin polymerization Also disclosed is a prepolymerized catalyst having an average particle diameter of from 500 to 5,000 μm, useful for olefin polymerization. An olefin is pre-polymerized in the presence of a metallocene catalyst component and a solid low bulk-density aluminoxane and, optionally, an organoaluminum compound.

13 Claims, 3 Drawing Sheets

*1 Prepolymerization in a liquid phase at an olefin partial pressure of not more than 4kg/cm$^2$-G \* 1 Prepolymerization under such condition that an average particle diameter be 50 to 50000μm and a bulk density be 0.01 to 0.2g/cc

SOLID ALUMINOXANE FOR CATALYST CARRIER, PROCESS FOR PREPARING THE SAME, AND USES THEREOF

FIELD OF THE INVENTION

The present invention relates to a solid aluminoxane for catalyst carrier, a process for preparing the same and uses thereof. More particularly, the invention relates to a low-bulk density solid aluminoxane for catalyst carrier, which is employable as an olefin polymerization catalyst component and/or a polymerization catalyst carrier, a process for preparing the solid aluminoxane, an olefin polymerization catalyst containing the solid aluminoxane, a prepolymerized catalyst for olefin polymerization containing the solid aluminoxane, an olefin polymerization process using any of those catalysts, and an olefin polymer obtained by the olefin polymerization process. The invention also relates to a process for preparing a prepolymerized catalyst for olefin polymerization wherein prepolymerized catalyst particles do not adhere to each other in the prepolymerization stage, a solid olefin polymerization catalyst component substantially containing no inorganic carrier, and an olefin polymerization process wherein an olefin is subjected to gas phase polymerization using the solid olefin polymerization catalyst component.

The meaning of the term "polymerization" used herein is not limited to "homopolymerization" but may comprehend "copolymerization". Also, the meaning of the term "polymer" used herein is not limited to "homopolymer" but may comprehend "copolymer".

BACKGROUND OF THE INVENTION

Olefin polymers, such as polyethylene, linear low-density polyethylene (LLDPE) which is a copolymer of ethylene and an α-olefin and an ethylene/propylene terpolymer (EPT), are widely used as film forming materials and industrial materials.

The olefin polymers are produced using Ziegler catalysts or metallocene catalysts. By virtue of recent improvements of transition metal catalysts for olefin polymerization, production capacity of an olefin polymer per unit quantity of the transition metal has been rapidly increased, and as a result, catalyst removal operation after the polymerization came to be omitted.

In particular, the metallocene catalysts are highly active and are known to exhibit excellent mechanical properties of the resulting polymer such as high transparency and surface non-tackiness because of narrow molecular weight distribution. Therefore, the catalysts are coming to be practically used in solution polymerization, slurry polymerization and gas phase polymerization.

When the metallocene catalyst is used as a solid catalyst for the slurry polymerization or the gas phase polymerization, there has been made an attempt to conduct olefin polymerization in a slurry polymerization system or a gas phase polymerization system using an inorganic carrier supported type solid catalyst wherein any one or both of a metallocene catalyst component and an aluminoxane are supported on a porous inorganic oxide carrier such as silica, silica/alumina or alumina.

However, if an olefin is polymerized or copolymerized in a slurry polymerization system or a gas phase polymerization system using the inorganic carrier supported type solid catalyst, the activity per unit weight of the catalyst becomes lower than that in the solution polymerization system, because silica or the like making no contribution to the activity is contained in the catalyst.

In the polymerization of an olefin using the inorganic carrier supported type solid catalyst, further, a polymer having a relatively high bulk density is obtained. In the gas phase polymerization or the slurry polymerization, polymerization is generally carried out in a state such that a polymer is present around the active site, differently from the solution polymerization. Hence, an ununiform polymer having a wide composition distribution and/or a wide molecular weight distribution is apt to be obtained. Especially in case of polymer particles hardly having voids in the particles, distribution of monomer concentration easily takes place because of low monomer diffusion into particles, whereby an ununiform polymer is apt to be obtained.

Moreover, in the preparation of a prepolymerized catalyst, prepolymerized catalyst particles occasionally adhere to each other or to a wall of the polymerization reactor.

OBJECT OF THE INVENTION

The present invention is intended to solve such problems associated with the prior art as described above, and it is an object of the invention to provide a low-bulk density solid aluminoxane applicable as a carrier of a polymerization catalyst and to provide an olefin polymerization catalyst component capable of forming a solid olefin polymerization catalyst having high polymerization activity and high voids by being combined with a metallocene catalyst component.

It is another object of the invention to provide an olefin polymer having a narrow composition distribution and/or a narrow molecular weight distribution and to provide an olefin polymer containing a large amount of a rubber in the range of elastomer.

It is a further object of the invention to provide a process for preparing a high-void prepolymerized catalyst for olefin polymerization wherein prepolymerized catalyst particles do not adhere to each other or to a wall of the polymerization reactor.

It is a still further object of the invention to provide a solid olefin polymerization catalyst component containing no inorganic carrier such as silica, a solid olefin polymerization catalyst component having high polymerization activity and capable of producing a uniform polymer, and an olefin polymerization process comprising subjecting an olefin to gas phase polymerization in the presence of the above catalyst component.

SUMMARY OF THE INVENTION

The solid aluminoxane for catalyst carrier according to the present invention is selected from the group consisting of an aluminoxane represented by the following formula (I), an aluminoxane represented by the following formula (II) and an aluminoxane having a recurring unit represented by the following formula (IIIa) and a recurring unit represented by the following formula (IIIb) and has a bulk density of 0.01 to 1.0

(I)

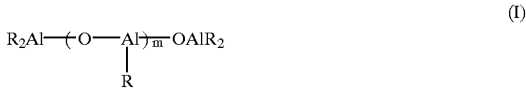

-continued

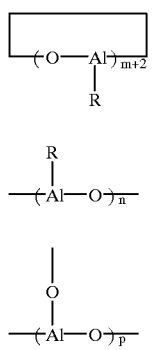

(II)

$$\fbox{$-\!\!\left(\!\!\begin{array}{c} O\!\!-\!\!Al\!-\!\! \\ | \\ R \end{array}\!\!\right)_{\!\!m+2}$}$$

(IIIa)

$$-\!\!\left(\!\!\begin{array}{c} R \\ | \\ Al\!-\!O \end{array}\!\!\right)_{\!\!n}\!\!-$$

(IIIb)

$$-\!\!\left(\!\!\begin{array}{c} | \\ O \\ | \\ Al\!-\!O \end{array}\!\!\right)_{\!\!p}\!\!-$$

wherein R is a hydrocarbon group of 1 to 10 carbon atoms, m is an integer of 2 to 500, and n and p are each an integer of 1 or more.

The solid aluminoxane for catalyst carrier preferably has an average particle diameter of 50 to 50,000 μm.

The solid aluminoxane for catalyst carrier can be obtained by bringing a solution of an aluminoxane having an alkyl group/aluminum atom ratio of not less than 1.5 into contact with a solvent insolubilizing or slightly solubilizing the aluminoxane to precipitate the aluminoxane in such a manner that at least 80% by weight based on the total amount of the aluminoxane to be precipitated is precipitated within 60 seconds from the beginning of precipitation.

The solid aluminoxane for catalyst carrier can be obtained also by causing a solution of an aluminoxane having an alkyl group/aluminum atom ratio of not less than 1.5 to react with water until the alkyl group/aluminum atom ratio of the aluminoxane becomes 1.0 to 1.5 to precipitate the aluminoxane.

In the above precipitation, the precipitation conditions are preferably controlled so that the average particle diameter of the solid aluminoxane becomes 50 to 50,000 μm.

The solid aluminoxane for catalyst carrier can be used as a n olefin polymerization catalyst component and/or a polymerization catalyst carrier by being combined with a metallocene catalyst component.

More specifically, the solid aluminoxane for catalyst carrier can be used in the form of a polymerization catalyst obtained by supporting a metallocene catalyst component (A) on the solid aluminoxane for catalyst carrier (B) or in the form of a prepolymerized catalyst obtained by prepolymerizing an olefin in the presence of the catalyst or in the presence of the catalyst and an organoaluminum compound (C).

The prepolymerized catalyst preferably has an average particle diameter of 50 to 50,000 μm and a bulk density of 0.01 to 0.2 g/cc.

The olefin polymerization process according to the present invention comprises polymerizing an olefin in the presence of the above-mentioned catalyst, preferably in a gas phase or a liquid phase of slurry.

The olefin polymer according to the present invention has an average particle diameter of 100 to 100,000 μm and a bulk density of 0.05 to 0.55 g/cc. The olefin polymer can be prepared by the above-mentioned olefin polymerization process.

The process for preparing a prepolymerized catalyst for olefin polymerization according to the present invention comprises polymerizing an olefin in a liquid phase under the condition of an olefin partial pressure of not more than 4 kg/cm²-G in the presence of:

(A) a metallocene catalyst component,
(B) an aluminoxane which is precipitated in the prepolymerization stage in an amount of not less than 80% by weight based on the whole amount of the aluminoxane present in the system, or an aluminoxane which has been already precipitated and is solid, and optionally
(C) an organoaluminum compound.

The aluminoxane which is precipitated in the prepolymerization stage in an amount of not less than 80% by weight based on the whole amount of the aluminoxane present in the system or the aluminoxane which has been already precipitated and is solid is, for example, the aforesaid solid aluminoxane.

The prepolymerized catalyst preferably has an average particle diameter of 50 to 50,000 μm and a bulk density of 0.01 to 0.2 g/cc.

The solid olefin polymerization catalyst component according to the present invention has an average particle diameter of 50 to 50,000 μm and a bulk density of 0.01 to 0.2 g/cc, and substantially consists of a polyolefin and an aluminoxane.

The total content of the polyolefin and the aluminoxane is preferably in the range of 90 to 100%.

The solid olefin polymerization catalyst component preferably contains no inorganic carrier.

The solid olefin polymerization catalyst component is obtained by, for example, prepolymerizing an olefin in the presence of a metallocene catalyst component and an aluminoxane.

The olefin polymerization process according to the present invention comprises subjecting an olefin to gas phase polymerization by the use of the solid olefin polymerization catalyst component.

DETAILED DESCRIPTION OF THE INVENTION

Figure 1:
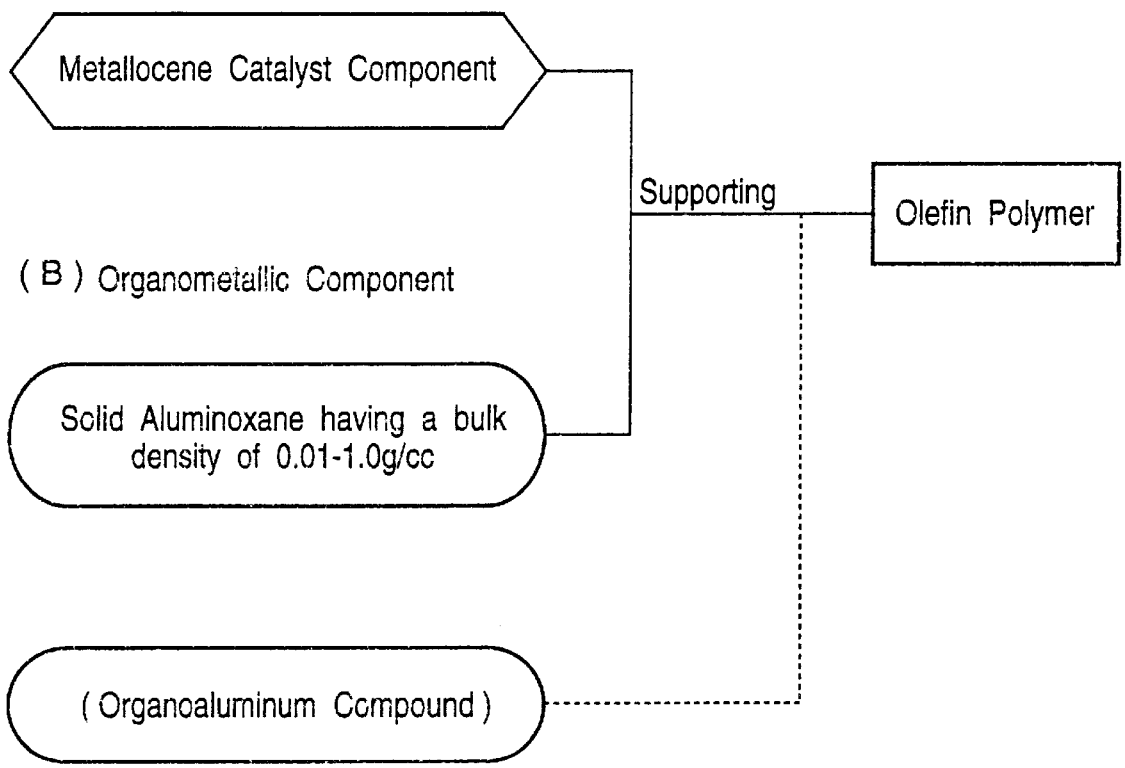
FIG. 1 is a flow chart illustrating one example of a process for preparing a catalyst containing a solid aluminoxane for catalyst carrier, said catalyst being used for the olefin polymerization shown by the present invention.
Figure 2:
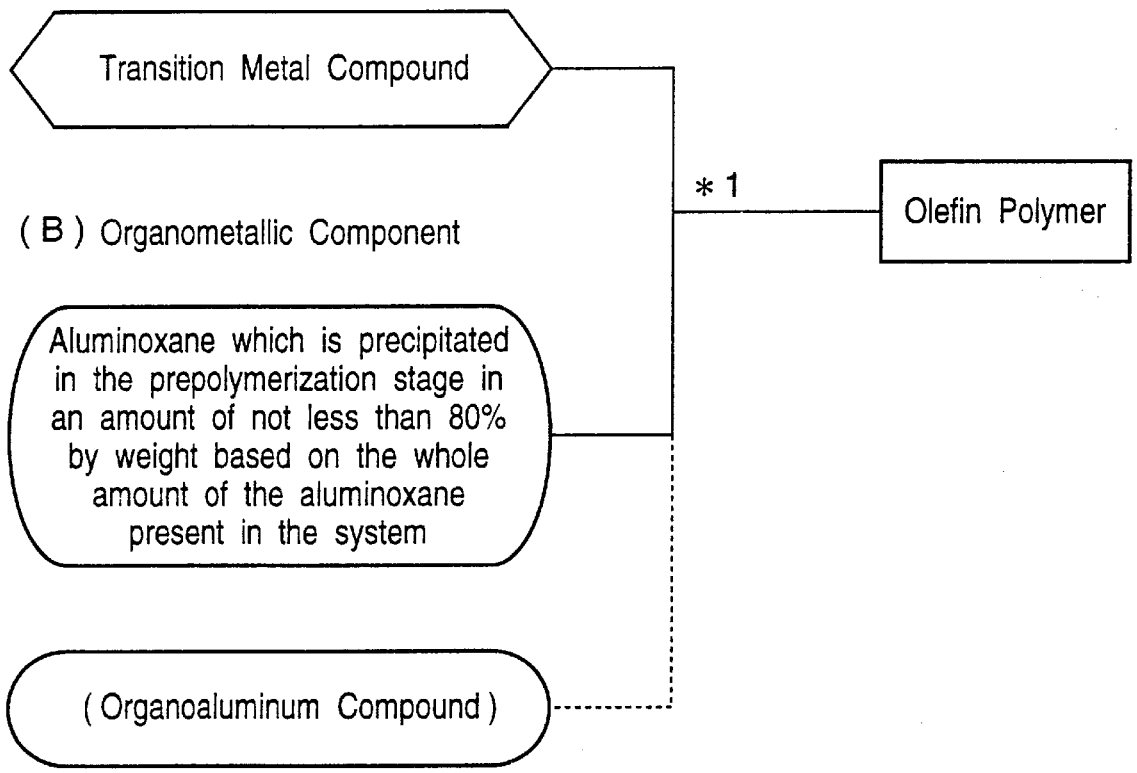
FIG. 2 is a flow chart illustrating one example of a process for preparing a prepolymerized catalyst for olefin polymerization, said prepolymerized catalyst being used for the olefin polymerization shown by the present invention.
Figure 3:
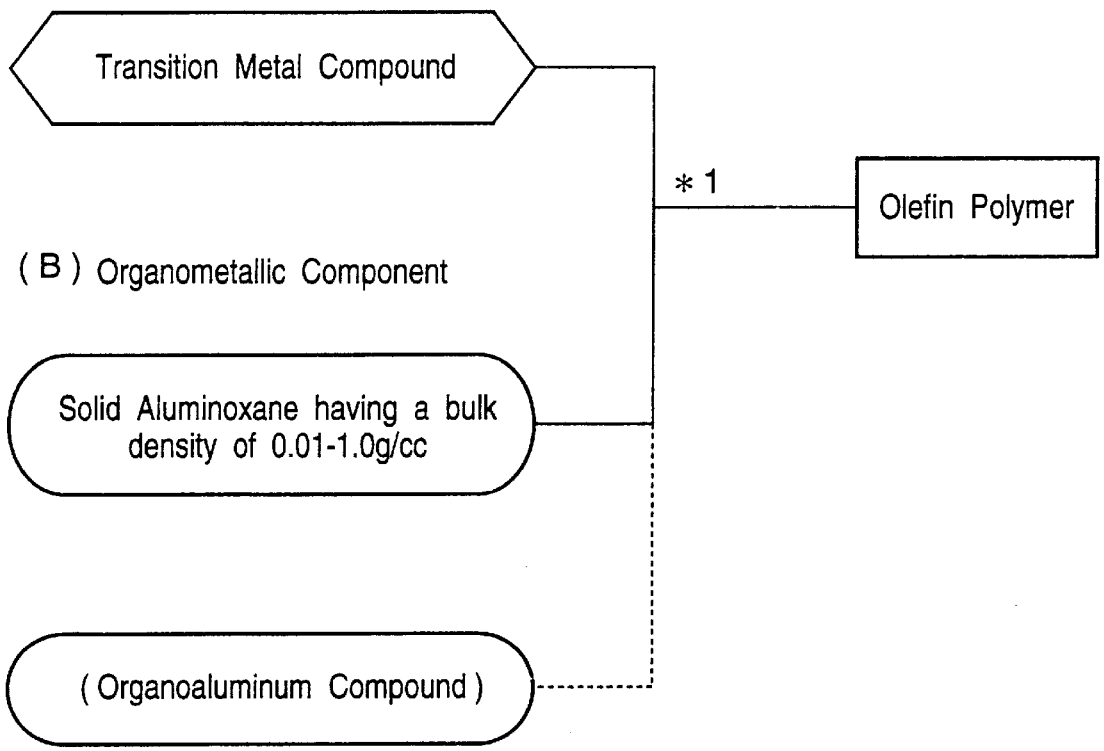
FIG. 3 is a flow chart illustrating one example of a process for preparing a catalyst containing a solid olefin polymerization catalyst component, said catalyst component being used for the olefin polymerization shown by the present invention.

The solid aluminoxane for catalyst carrier according to the invention, the process for preparing the solid aluminoxane and the uses of the solid aluminoxane are described in detail hereinafter.

Solid Aluminoxane for Catalyst Carrier

The solid aluminoxane for catalyst carrier according to the invention is an aluminoxane selected from the group consisting of an aluminoxane represented by the following formula (I), an aluminoxane represented by the following formula (II) and an aluminoxane having a recurring unit represented by the following formula (IIIa) and a recurring unit represented by the following formula (IIIb);

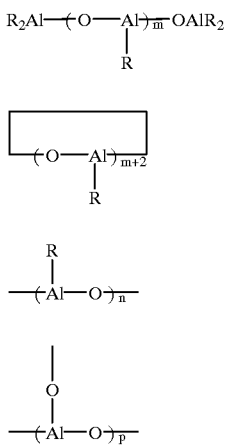

$$R_2Al-(O-Al)_{\overline{m}}-OAlR_2 \quad (I)$$
$$\phantom{R_2Al-(O-Al)_{\overline{m}}}|$$
$$\phantom{R_2Al-(O-Al)_{\overline{m}}}R$$

$$\left[-(O-Al)_{\overline{m+2}}\right] \quad (II)$$
$$\phantom{-(O-Al)}|$$
$$\phantom{-(O-Al)}R$$

$$\begin{array}{c} R \\ | \\ -(Al-O)_{\overline{n}}- \end{array} \quad (IIIa)$$

$$\begin{array}{c} | \\ O \\ | \\ -(Al-O)_{\overline{p}}- \end{array} \quad (IIIb)$$

wherein R is a hydrocarbon group of 1 to 10 carbon atoms, preferably 1 to 4 carbon atoms. Examples of the hydrocarbon groups include methyl, ethyl, propyl, isopropyl, isopropenyl, n-butyl, sec-butyl, tert-butyl, pentyl, hexyl, octyl, decyl, dodecyl, tridecyl, tetradecyl, hexadecyl, octadecyl, eicosyl, cyclohexyl, cyclooctyl, phenyl, tolyl and ethylphenyl. Of these, preferable are methyl, ethyl and isobutyl, and particularly preferable is methyl.

m is an integer of 2 to 500, preferably 6 to 300, particularly preferably 10 to 100.

n and p are each an integer of 1 or more. The aluminoxane having a recurring unit represented by the formula (IIIa) and a recurring unit represented by the formula (IIIb) preferably has a molecular weight, as measured by cryoscopy in benzene, of 200 to 2,000.

The solid aluminoxane may be a halogenated aluminoxane wherein a part of R is substituted with a halogen atom such as chlorine or bromine and the halogen content is not more than 40% by weight.

The solid aluminoxane of the invention has a bulk density of 0.01 to 1.0 g/cc, preferably 0.02 to 0.5 g/cc, more preferably 0.02 to 0.45 g/cc, still more preferably 0.02 to 0.43 g/cc. The solid aluminoxane has void percentage of usually 50 to 98%, preferably 60 to 95%, particularly preferably 70 to 90%, and the solid aluminoxane of the invention is porous.

If the bulk density of the solid aluminoxane is less than 0.01 g/cc, the strength of the solid aluminoxane is lowered, and thereby the aluminoxane particles are deformed by degradation or external force or the particle properties are deteriorated when the aluminoxane is used in the gas phase polymerization or the slurry polymerization. If the bulk density thereof is larger than 1.0 g/cc, the void percentage of the polymer particles during the polymerization is lowered, and thereby an ununiform polymer is easily produced or the aluminoxane has low surface area and shows low activity.

The bulk density of the solid aluminoxane can be determined in the following manner. An aluminoxane slurry prepared in a solvent is vacuum dried at room temperature to remove the solvent, and the remainder is filled in a container having a capacity of 1 cc, followed by measuring the weight. The bulk density of the later-described solid catalyst and prepolymerized catalyst is also measured in this manner.

The solid aluminoxane of the invention has an aluminum volume concentration in n-hexane, as measured by the below-described method, of usually 0.02 to 1.0 mmol/cc, preferably 0.04 to 0.5 mmol/cc, particularly preferably 0.05 to 0.2 mmol/cc.

The aluminum volume concentration in n-hexane is measured in the following manner. A given amount of a n-hexane slurry of a solid aluminoxane is introduced into a volume-measurable container (e.g., measuring cylinder) in a nitrogen atmosphere. The amount of the aluminoxane introduced is measured before or after the introduction to determine the total number of moles of aluminum introduced. The amount of the solid aluminoxane introduced can be properly selected, as far as the sedimentation slurry volume (described later) is measurable with an error of ±0.1 vol %. After the introduction, the n-hexane slurry of solid aluminoxane is allowed to stand for 24 hours or more, and the interface between the sedimented slurry and the supernatant is confirmed by visual observation to measure the volume of the sedimented slurry (sedimentation slurry volume). The number of moles of aluminum in the solid aluminoxane introduced is divided by the volume of the sedimented slurry, and the obtained value is taken as the aluminum volume concentration in n-hexane.

The solid aluminoxane of the invention has an average particle diameter of usually 50 to 50,000 μm, preferably 200 to 10,000 μm, particularly preferably 500 to 5,000 μm.

The average particle diameter of the solid aluminoxane was determined by a method comprising observing particles of the aluminoxane by a scanning electron microscope, measuring diameters of 100 or more particles and weight averaging them.

The diameter of each particle of the solid aluminoxane was determined by measuring the Pythagorean method maximum length from the particle image. That is, the particle image was interposed between two parallel lines in each of the horizontal direction and the vertical direction to measure the length in each direction, and the particle diameter was calculated from the following formula.

Particle diameter=$((\text{Horizontal length})^2+(\text{Vertical length})^2)^{0.5}$ The weight average particle diameter was calculated from the following formula using the above-obtained article diameters.

Average particle diameter=$\Sigma nd^4/\Sigma nd^3$ wherein n is the number of particles and d is a particle diameter.

The average particle diameter of the later-described solid catalyst and prepolymerized catalyst is also measured in this manner.

The proportion of the amount of the solid aluminoxane of the invention dissolved in n-hexane maintained at 25° C. (dissolution proportion in n-hexane) is in the range of usually 0 to 40% by mol, preferably 0 to 20% by mol. particularly preferably 0 to 10% by mol.

The dissolution proportion of the solid aluminoxane in n-hexane was determined in the following manner. To 50 ml of n-hexane maintained at 25° C., 2 g of a solid aluminoxane carrier was added, and they were stirred for 2 hours. Then, the solution portion was separated using a G-4 glass filter, and the aluminum concentration in this filtrate was measured. Accordingly, the dissolution proportion of the aluminoxane is defined as a proportion of the aluminum atom present in the filtrate to the quantity of the aluminum atom corresponding to 2 g of the aluminoxane used.

The solid aluminoxane of the invention can be prepared by a process comprising preparing a solution of an aluminoxane and then precipitating the aluminoxane under given conditions.

The solution of an aluminoxane (aluminoxane solution) is formed from at least an aluminoxane and a solvent capable of dissolving the aluminoxane. The aluminoxane solution can be obtained by, for example, merely mixing the both components or mixing the both components under heating. The aluminoxane solution may be prepared by the following processes.

(1) A trialkylaluminum is added to a hydrocarbon medium suspension of a compound containing adsorbed water or a salt containing water of crystallization, e.g., magnesium chloride hydrate, copper sulfate hydrate, aluminum sulfate hydrate, nickel sulfate hydrate or cerous chloride, to react them.

(2) Water is allowed to directly act on a trialkylaluminum in a medium such as benzene, toluene, ethyl ether or tetrahydrofuran.

The processes (1) and (2) may be successively used in combination. The aluminoxane solution may contain a small amount of an organometallic component. For example, an organometallic compound component such as a halogen-containing organoaluminum compound or an organomagnesium compound may be allowed to be present together with the trialkylaluminum.

From the thus obtained aluminoxane solution, the aluminoxane is precipitated under given conditions, whereby the solid aluminoxane of the invention can be prepared. For example, the aluminoxane solution is contacted with a solvent insolubilizing or slightly solubilizing the aluminoxane, or the ratio of the alkyl group to the aluminum atom (alkyl group/aluminum atom) in the aluminoxane is varied to the specific value to make the aluminoxane insoluble, whereby the solid aluminoxane is precipitated in the suspended state.

In more detail, a solvent incapable of dissolving or capable of slightly dissolving the aluminoxane is added to the aluminoxane solution and they are stirred to contact with each other, or the aluminoxane solution is added to a solvent incapable of dissolving or capable of slightly dissolving the aluminoxane and they are stirred to contact with each other, whereby the solid aluminoxane is precipitated in the suspended state. The solid aluminoxane may be obtained by adding water to the aluminoxane in the dissolved state to decrease the alkyl group/aluminum atom ratio.

Any other processes are available, as far as the conditions of the processes can ensure the properties of the solid aluminoxane.

In the contact of the aluminoxane solution with the solvent insolubilizing or slightly solubilizing the aluminoxane, it is preferable that 80% by weight of the aluminoxane based on the whole amount of the aluminoxane to be precipitated is precipitated within 60 seconds from the beginning of the precipitation.

The aluminoxane thus obtained may be used as not a carrier but a catalyst component serving as a mere co-catalyst.

In the contact of the aluminoxane solution with the solvent incapable of dissolving or capable of slightly dissolving the aluminoxane, there is no specific limitation on the concentration of the aluminoxane solution, but the concentration is in the range of usually 0.01 to 2.0 mol/l, preferably 0.1 to 0.5 mol/l.

In the contact of the aluminoxane solution with the solvent insolubilizing or slightly solubilizing the aluminoxane, the proportion of the solvent insolubility or slightly solubilizing the aluminoxane to 100 parts by weight of the aluminoxane solution is in the range of usually 100 to 10,000 parts by weight, preferably 500 to 5,000 parts by weight, and the temperature is in the range of −100 to 100° C., preferably −50 to 70° C., particularly preferably −30 to 50° C. The contact is generally carried out under stirring.

The type of the solvent capable of dissolving or capable of slightly dissolving the aluminoxane is selected according to the properties of the aluminoxane. Examples of the solvents solubilizing the aluminoxane having methyl as R in the aforesaid formula (I), (II) or (IIIa) and having an alkyl group/aluminum atom ratio of not less than 1.5 include aromatic hydrocarbons, such as benzene, toluene, ethylbenzene, propylbenzene, butylbenzene, xylene and chlorobenzene.

As the solvent insolubilizing or slightly solubilizing the aluminoxane, a saturated hydrocarbon solvent is generally employed. Examples of such solvents include straight-chain or branched aliphatic hydrocarbons, such as pentane, hexane, decane, dodecane, kerosine and cyclohexane; and alicyclic hydrocarbons, such as cyclohexane, norbornane and ethylcyclohexane. As the solvent insolubilizing or slightly solubilizing the aluminoxane, a solvent having a higher boiling point than that of the solvent which is capable of dissolving the aluminoxane and used for preparing the aluminoxane solution is preferably employed.

In order to obtain the solid aluminoxane by decreasing the ratio of the alkyl group to the aluminum atom (i.e., alkyl group/aluminum atom ratio), a method of allowing water to directly act on the aluminoxane in the dissolved state can be exemplified. In detail, water is introduced into the solution of an aluminoxane having an alkyl group/aluminum atom ratio of not less than 1.5 to cause the aluminoxane to react with water, whereby the alkyl group/aluminum atom ratio in the aluminoxane after the reaction is decreased to precipitate the aluminoxane.

In the reaction of the aluminoxane with water, the concentration of the aluminoxane solution is not specifically limited, but it is in the range of usually 0.01 to 2.0 mol/l, preferably 0.1 to 0.5 mol/l.

The reaction of the aluminoxane with water is carried out so that the alkyl group/aluminum atom ratio in the aluminoxane after the reaction becomes usually 0.5 to 1.5, preferably 0.9 to 1.5, more preferably 1.0 to 1.5, particularly preferably 1.1 to 1.3. The reaction temperature is in the range of −100 to 100° C., preferably −50 to 70° C., particularly preferably −30 to 50° C. The contact of the aluminoxane with water is generally conducted under stirring, and is desirably conducted in a state where water is dispersed as homogeneously as possible. In order to accelerate dispersing of water, a method of introducing water vapors into an inert gas and bubbling the inert gas in the aluminoxane solution can be exemplified. Also available is a method wherein the aluminoxane having reacted with water is mixed with a fresh aluminoxane to cause the aluminoxane to react with water in such a manner that the alkyl group/aluminum atom ratio becomes 0.5 to 1.5.

In this method, a solvent, which can dissolve the aluminoxane when the alkyl group/aluminum atom ratio is high but precipitates the aluminoxane when the alkyl group/aluminum atom ratio becomes not more than 1.5, is desirably employed. For example, an aluminoxane wherein R in the aforesaid formula (I), (II) or (IIIa) is a mixed alkyl group of methyl and i-butyl having a ratio of 7:3 (methyl:i-butyl) and the ratio of all of the alkyl groups to the aluminum atoms is 1.7 is soluble in hexane, but when the alkyl group/aluminum atom ratio becomes 1.5 by the reaction with water, the aluminoxane is precipitated.

The above-mentioned processes to prepare the solid aluminoxane are mere examples, and the invention is in no way limited to those examples.

Olefin Polymerization Catalyst

The solid aluminoxane of the invention is used as an olefin polymerization catalyst component (carrier and/or co-catalyst). Particularly, a porous solid catalyst formed from the solid aluminoxane component of the invention and a metallocene catalyst component exhibits extremely high activity even when it is applied to olefin polymerization using any of a suspension polymerization process and a gas phase polymerization process. Especially in the gas phase polymerization process, the catalyst exhibits high activity and can produce a uniform polymer. Further, a polymer containing a large amount of a rubber in the range of elastomer can be obtained. It is highly important that the polymer in the range of elastomer can be efficiently obtained even in a gas phase or in a slurry state though this has been hitherto difficult.

An embodiment of the solid catalyst formed from the solid aluminoxane of the invention and a metallocene catalyst component is a catalyst comprising the solid aluminoxane component and a metallocene catalyst component supported thereon.

Examples of processes for preparing a solid catalyst by supporting the metallocene catalyst component on the solid aluminoxane component include (1) a process comprising supporting the metallocene catalyst component on the solid aluminoxane temporarily prepared and (2) a process comprising adding the metallocene catalyst component in the step of forming the solid aluminoxane component to support the metallocene catalyst component on the solid aluminoxane successively to or simultaneously with the formation of the solid aluminoxane.

The process (2) is described below in detail. As the process (2), there can be mentioned, for example, (2-(1)) a process wherein a solution of an aluminoxane is contacted with a solvent insolubilizing or slightly solubilizing the aluminoxane to precipitate a solid aluminoxane in the suspended state and thereby form a suspension of the solid aluminoxane, and the suspension of the solid aluminoxane is contacted with a solution of a metallocene catalyst component; and (2-(2)) a process wherein water is introduced into a solution of an aluminoxane to vary the alkyl group/aluminum atom ratio to not more than 1.5, whereby a solid aluminoxane is precipitated in the suspended state to form a suspension of the solid aluminoxane, and the suspension of the solid aluminoxane is contacted with a solution of a metallocene catalyst component.

In each of the above processes, other catalyst components such as the later-described electron donor and organoaluminum compound may be added in any stage.

The solid catalyst prepared by the use of the solid aluminoxane has a bulk density of 0.01 to 1.0 g/cc, preferably 0.02 to 0.5 g/cc, more preferably 0.02 to 0.45 g/cc, particularly preferably 0.02 to 0.43 g/cc.

The olefin polymerization solid catalyst has an average particle diameter of 50 to 50,000 $\mu$m, preferably 200 to 10,000 $\mu$m, more preferably 500 to 5,000 $\mu$m.

Prepolymerized Catalyst

The catalyst formed from the solid aluminoxane of the invention and the metallocene catalyst component may be a prepolymerized catalyst obtained by prepolymerizing an olefin. The prepolymerization is carried out in the presence of the above-described solid catalyst in the absence of a solvent or in an inert hydrocarbon medium, and from the viewpoint of ease of operation, the prepolymerization is preferably carried out in an inert hydrocarbon medium.

Examples of the inert hydrocarbon solvents include aliphatic hydrocarbons, such as butane, isobutane, pentane, hexane, octane, decane, dodecane, hexadecane and octadecane; alicyclic hydrocarbons, such as cyclopentane, methylcyclopentane, cyclohexane and cyclooctane; and petroleum fractions, such as kerosine and gas oil.

Examples of the olefins employable for the prepolymerization include $\alpha$-olefins of 2 to 20 carbon atoms, such as ethylene, propylene, 1-butene, 4-methyl-1-pentene, 1-hexene, 1-octene, 1-decene, 1-dodecene and 1-tetradecene. These $\alpha$-olefins can be used singly or in combination of two or more kinds. Of these, single use of ethylene or use of ethylene and a small amount of another $\alpha$-olefin in combination is preferable.

In the prepolymerization, the concentration of the solid catalyst in the prepolymerization reaction system is in the range of usually $10^{-6}$ to 1 g·atom/l, preferably $10^{-4}$ to $10^{-2}$ g·atom/l, in terms of a concentration of the transition metal atom in the solid catalyst. The ratio of the transition metal (M) in the metallocene catalyst component to the aluminum atom (Al) in the solid aluminoxane (M/Al) is in the range of usually 0.001 to 0.2, preferably 0.002 0.05, more preferably 0.005 to 0.02.

The prepolymerization temperature is in the range of –20 to 70° C., preferably –10 to 60° C., more preferably 0 to 50° C. The prepolymerization can be carried out batchwise or continuously, and can be carried out at atmospheric pressure or under pressure.

The prepolymerization may be conducted in the presence of a molecular weight modifier such as hydrogen, but it is preferable that the amount of the molecular weight modifier is controlled so that a prepolymer having an intrinsic viscosity ($\eta$), as measured in decalin at 135° C., of not less than 0.2 dl/g, preferably 0.5 to 20 dl/g, can be produced.

In the preparation of the prepolymerized catalyst, other catalyst components such as the later-described electron donor and aluminum compound may be added.

In the prepolymerized catalyst for olefin polymerization obtained above, the $\alpha$-olefin is desirably polymerized in an amount of 1 to 50,000 g, preferably 10 to 20,000 g, more preferably 100 to 15,000 g, particularly preferably 100 to 10,000 g, based on 1 mg·atom of the metallocene catalyst component in the solid catalyst. The average particle diameter of the prepolymerized catalyst is in the range of 50 to 80,000 $\mu$m, preferably 500 to 5,000 $\mu$m, and the bulk density thereof is in the range of preferably 0.01 to 0.2 g/cc.

Metallocene Catalyst Component

As the metallocene catalyst component for the above-described catalyst, any compound can be used, as far as it has catalytic ability. In general, a transition metal compound represented by the following formula (IV) or (V) is employed.

$$ML_x \tag{IV}$$

wherein M is a transition metal atom selected from Group 4 of the periodic table, and is specifically selected from the group consisting of titanium, zirconium and hafnium. Of these, preferable are titanium and zirconium, and particularly preferable is zirconium.

L is a ligand coordinated to the transition metal atom, at least one ligand L is a ligand having cyclopentadienyl skeleton, and L other than the ligand having cyclopentadienyl skeleton is a hydrocarbon group of 1 to 12 carbon atoms, an alkoxy group, an aryloxy group, a trialkylsilyl group, a —SO₃R group (R is a hydrocarbon group of 1 to 8 carbon atoms which may have a substituent such as halogen), a halogen atom or a hydrogen atom. x is a valence of the transition metal atom.

An example of the transition metal compound represented by the formula (IV) is a zirconium compound containing a ligand having cyclopentadienyl skeleton. Such a zirconium compound is, for example, a compound represented by the following formula (IV'):

  (IV')

wherein $R^1$ is a ligand having cyclopentadienyl skeleton; $R^2$, $R^3$ and $R^4$ are each a ligand having cyclopentadienyl skeleton, an aryl group, an alkyl group, a cycloalkyl group, an aralkyl group, a halogen atom, hydrogen, $OR^a$, $SR^b$, $NR^c_2$ or $PR^d_2$; $R^a$, $R^b$, $R^c$ and $R^d$ are each a hydrocarbon group, such as an alkyl group, a cycloalkyl group, an aryl group or an aralkyl group, or a silyl group; two of $R^c$ or two of $R^d$ may be linked to form a ring; $k \geq 1$; and $k+l+m+n=4$.

Examples of the ligands having cyclopentadienyl skeleton include cyclopentadienyl, methylcyclopentadienyl, ethylcyclopentadienyl, dimethylcyclopentadienyl, indenyl, tetrahydroindenyl and fluorenyl. Examples of the alkyl groups include methyl, ethyl, propyl, isopropyl, butyl, hexyl, octyl, 2-ethylhexyl, decyl and oleyl. Examples of the aryl groups include phenyl and tolyl. Examples of the aralkyl groups include benzyl and neophyl. Examples of the cycloalkyl groups include cyclopentyl, cyclohexyl, cyclooctyl, norbornyl, bicyclononyl and these groups substituted with alkyl groups. Also available are unsaturated aliphatic groups, such as a vinyl group, an allyl group, a propenyl group, an isopropenyl group and a 1-butenyl group; and unsaturated alicyclic groups, such as a cyclohexenyl group. Examples of the halogen atoms include fluorine, chlorine and bromine.

Examples of zirconium compounds represented by the formula (IV) include bis(cyclopentadienyl)zirconium monochloride monohydride, bis(cyclopentadienyl)zirconium monobromide monohydride, bis(cyclopentadienyl)methylzirconium hydride,
bis(cyclopentadienyl)ethylzirconium hydride,
bis(cyclopentadienyl)cyclohexylzirconium hydride,
bis(cyclopentadienyl)phenylzirconium hydride,
bis(cyclopentadienyl)benzylzirconium hydride,
bis(cyclopentadienyl)neopentylzirconium hydride,
bis(methylcyclopentadienyl)zirconium monochloride monohydride, bis(indenyl)zirconium monochloride monohydride, bis(cyclopentadienyl)zirconium dichloride,
bis(cyclopentadienyl)zirconium dibromide,
bis(cyclopentadienyl)methylzirconium monochloride,
bis(cyclopentadienyl)ethylzirconium monochloride,
bis(cyclopentadienyl)cyclohexylzirconium monochloride,
bis(cyclopentadienyl)phenylzirconium monochloride,
bis(cyclopentadienyl)benzylzirconium monochloride,
bis(methylcyclopentadienyl)zirconium dichloride,
bis(pentamethylcyclopentadienyl)zirconium dichloride,
bis(indenyl)zirconium dichloride, bis(indenyl)zirconium dibromide, bis(cyclopentadienyl)zirconium diphenyl,
bis(cyclopentadienyl)zirconium dibenzyl,
bis(cyclopentadienyl)methoxyzirconium chloride,
bis(cyclopentadienyl)ethoxyzirconium chloride,
bis(cyclopentadienyl)butoxyzirconium chloride,
bis(cyclopentadienyl)-2-ethylhexoxyzirconium chloride,
bis(cyclopentadienyl) methyzirconium ethoxide,
bis(cyclopentadienyl)methylzirconium butoxide,
bis(cyclopentadienyl)phenylzirconium ethoxide,
bis(cyclopentadienyl)benzylzirconium ethoxide,
bis(methylcyclopentadienyl)ethoxyzirconium chloride,
bis(indenyl)ethoxyzirconium chloride,
bis(cyclopentadienyl)ethoxyzirconium,
bis(cyclopentadienyl)butoxyzirconium,
bis(cyclopentadienyl)-2-ethylhexoxyzirconium,
bis(cyclopentadienyl)phenoxyzirconium chloride,
bis(cyclopentadienyl)cyclohexoxyzirconium chloride,
bis(cyclopentadienyl)phenylmethoxyzirconium chloride,
bis(cyclopentadienyl)methylzirconiumphenyl methoxide,
bis(cyclopentadienyl)trimethylsiloxyzirconium chloride,
bis(cyclopentadienyl)triphenylsiloxyzirconium chloride,
bis(cyclopentadienyl)thiophenylzirconium chloride,
bis(cyclopentadienyl)thioethylzirconium chloride,
bis(cyclopentadienyl)bis(dimethylamido)zirconium,
bis(cyclopentadienyl)diethylamidozirconium chloride,
ethylenebis(indenyl)ethoxyzirconium chloride,
ethylenebis(4,5,6,7-tetrahydro-1-indenyl) ethoxyzirconium chloride, ethylenebis(indenyl) dimethylzirconium,
ethylenebis(indenyl)dimethylzirconium,
ethylenebis(indenyl)diphenylzirconium,
ethylenebis(indenyl)dibenzylzirconium,
ethylenebis (indenyl )methyl zirconium monobromide,
ethylenebis(indenyl) ethylzirconium monochloride,
ethylenebis(indenyl)benzylzirconium monochloride,
ethylenebis(indenyl)methylzirconium monochloride,
ethylenebis(indenyl) zirconium dichioride,
ethylenebis(indenyl) zirconium dibromide,
ethylenebis(4,5,6,7-tetrahydro-1-indenyl) dimethylzirconium,
ethylenebis (4,5,6,7-tetrahydro-1-indenyl) methylzirconium monochloride,
ethylenebis(4,5,6,7-tetrahydro-1-indenyl)zirconium dichloride,
ethylenebis(4,5,6,7-tetrahydro-1-indenyl)zirconium dibromide,
ethylenebis(4-methyl-1-indenyl)zirconium dichloride,
ethylenebis(5-methyl-1-indenyl) zirconium dichloride,
ethylenebis(6-methyl-1-indenyl)zirconium dichloride,
ethylenebis(7-methyl-1-indenyl)zirconium dichloride,
ethylenebis(5-methoxy-1-indenyl)zirconium dichloride,
ethylenebis(2,3-dimethyl-1-indenyl)zirconium dichloride,
ethylenebis(4,7-dimethyl-1-indenyl)zirconium dichloride,
ethylenebis(4,7-dimethoxy-1-indenyl)zirconium dichloride,
ethylenebis(indenyl)zirconium dimethoxide,
ethylenebis(indenyl)zirconium diethoxide,
ethylenebis(indenyl)methoxyzirconium chloride,
ethylenebis(indenyl)ethoxyzirconium chloride,
ethylenebis(indenyl)methylzirconium ethoxide, ethylenebis(4,5,6,7-tetrahydro-1-indenyl)zirconium dimethoxide, ethylenebis(4,5,6,7-tetrahydro-1-indenyl)zirconium diethoxide, ethylenebis(4,5,6,7-tetrahydro-1-indenyl) methoxyzirconium chloride, ethylenebis(4,5,6,7-tetrahydro-1-indenyl) ethoxyzirconium chloride and ethylenebis(4,5,6,7-tetrahydro-1-indenyl) methylzirconium ethoxide.

Compounds wherein the ethylene crosslinked parts are replaced with alkylene crosslinked parts such as isopropylidene, diphenylmethylene and methylphenylmethylene in the above compounds can be also exemplified. Further, compounds wherein the ethylene crosslinked parts are replaced with silicon atom crosslinked parts such as dimethylsilylene, methylphenylsilylene and diphenylsilylene in the above compounds can be also exemplified.

Examples of titanium compounds represented by the formula (IV) include bis(cyclopentadienyl)titanium monochloride monohydride, bis(cyclopentadienyl)methyltitanium hydride, bis(cyclopentadienyl)phenyltitanium chloride, bis(cyclopentadienyl)benzyltitanium chloride, bis(cyclopentadienyl)titanium chloride, bis(cyclopentadienyl)titanium dibenzyl, bis(cyclopentadienyl)ethoxytitanium chloride, bis(cyclopentadienyl)butoxytitanium chloride, bis(cyclopentadienyl)methyltitanium ethoxide, bis(cyclopentadienyl)phenoxytitanium chloride, bis(cyclopentadienyl)trimethylsiloxytitanium chloride, bis(cyclopentadienyl)thiophenyltitanium chloride, bis(cyclopentadienyl)bis(dimethylamido)titanium, bis(cyclopentadienyl)ethoxytitanium, ethylenebis(indenyl)titanium dichloride and ethylenebis(4,5,6,7-tetrahydro-1-indenyl)titanium dichloride.

Examples of hafnium compounds represented by the formula (IV) include bis(cyclopentadienyl)hafnium monochloride monohydride, bis(cyclopentadienyl)ethylhafnium monohydride, bis(cyclopentadienyl)phenylhafnium chloride, bis(cyclopentadienyl)hafnium dichloride, bis(cyclopentadienyl)hafnium dibenzyl, bis(cyclopentadienyl)ethoxyhafnium chloride, bis(cyclopentadienyl)butoxyhafnium chloride, bis(cyclopentadienyl)methylhafnium ethoxide, bis(cyclopentadienyl)phenoxyhafnium chloride, bis(cyclopentadienyl)thiophenylhafnium chloride, bis(cyclopentadienyl)bis(diethylamido)hafnium, ethylenebis(indenyl)hafnium dichloride and ethylenebis(4,5,6,7-tetrahydro-1-indenyl)hafnium dichloride.

Next, the transition metal compound represented by the formula (V) is described.

$$L^1MX_2 \quad (V)$$

wherein M is a transition metal selected from Group 4 of the periodic table, $L^1$ is a derivative of a delocalized π-bond group and imparts a restraint geometric shape to the active site of the metal M, and each X is the same or different and is a hydrogen atom, a halogen atom, a hydrocarbon group having 20 or less carbon atoms, a silyl group having 20 or less silicon atoms or a germyl group having 20 or less germanium atoms.

Of the compounds represented by the formula (V), preferable is a transition metal compound represented by the following formula (V'):

wherein M is titanium, zirconium or hafnium,

X is the same as described above,

Cp is π-bonded to M and is a cyclopentadienyl group having a substituent Z,

Z is oxygen, sulfur, boron or an element of Group 14 of the periodic table (e.g., silicon, germanium or tin), Y is a ligand containing nitrogen, phosphorus, oxygen or sulfur, and Z and Y may together form a condensed ring.

Examples of the compounds represented by the formula (V') include dimethylsilylene(t-butylamido)(tetramethyl-$\eta^5$-cyclopentadienyl)titanium dichloride and ((t-butylamido)(tetramethyl-$\eta^5$-cyclopentadienyl)-1,2-ethanediyl)titanium dichloride.

The metallocene compounds mentioned above can be used singly or in combination of two or more kinds.

Other Catalyst Components

In the polymerization of an olefin using the olefin polymerization catalyst of the invention, an electron donor, an organoaluminum compound, etc. are employable.

Examples of the electron donors include carboxylic acids, esters, ethers, ketones, aldehydes, alcohols, phenols, acid amides, oxygen-containing compounds such as compounds containing a metal atom—O—C bond (metal atom: aluminum, silicon, etc.), nitrites, amines and phosphines. The electron donor is used in an amount of usually not more than 1 mol, preferably 0.1 to 0.6 mol, based on 1 g·atom of the transition metal atom (M) in the metallocene catalyst component.

In the polymerization, in addition to the aforesaid solid aluminoxane on which the metallocene catalyst component is supported, there can be employed a solid aluminoxane on which no metallocene catalyst component is supported and which is the same as or different from the aforesaid solid aluminoxane, a liquid aluminoxane, or an organoaluminum compound represented by the following formula:

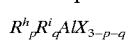

wherein $R^h$ is a hydrocarbon group of 1 to 10 carbon atoms (preferably an alkyl group of 1 to 6 carbon atoms, an alkenyl group, a cycloalkyl group or an aryl group), $R^i$ is an alkoxy group of 1 to 6 carbon atoms or an aryloxy group, X is a halogen atom, $3 \geq p > 0$, and $2 \geq q \geq 0$.

In particular, addition of an organoaluminum compound having a branched chain group such as triisobutylaluminum or isoprenylaluminum contributes to improvement of the polymerization activity.

In the polymerization, further, the below-described ionizing ionic compound is also employable. The ionizing ionic compound is a compound which reacts with the metallocene catalyst component to form an ion pair. Examples of the ionizing ionic compounds include Lewis acid, ionic compounds, borane compounds and carborane compounds.

The Lewis acid is, for example, a compound represented by the formula $BR_3$ (R is a phenyl group which may have a substituent such as fluorine, methyl or trifluoromethyl, or a fluorine atom). Examples of such compounds include trifluoroboron, triphenylboron, tris(4-fluorophenyl)boron, tris(3,5-difluorophenyl)boron, tris(4-fluoromethylphenyl) boron, tris(pentafluorophenyl)boron, tris(p-tolyl)boron, tris (o-tolyl)boron and tris(3,5-dimethylphenyl)boron.

Examples of the ionic compounds include trialkyl-substituted ammonium salts, N,N,-dialkylanilinium salts, dialkylammonium salts and triarylphosphonium salts. Particular examples of the trialkyl-substituted ammonium salts include triethylammoniumtetra(phenyl)boron, tripropylammoniumtetra(phenyl)boron and tri(n-butyl) ammoniumtetra(phenyl)boron. Particular examples of the dialkylammonium salts include di(1-propyl)ammoniumtetra (pentafluorophenyl)boron and dicyclohexylammoniumtetra (phenyl)boron. Moreover, triphenylcarbeniumtetrakis (pentafluorophenyl)borate, N,N-dimethylaniliniumtetrakis (pentafluorophenyl)borate and ferroceniumtetra (pentafluorophenyl)borate are also available as the ionic compounds.

Examples of the borane compounds include decaborane (14), bis[tri(n-butyl)ammonium]nonaborate, bis[tri(n-butyl) ammonium]decaborate, and salts of metallic borane anions such as bis[tri(n-butyl)ammonium]bis (dodecahydrododecaborate)-nickelate(III).

Examples of the carborane compounds include 4-carbanonaborane(14), 1,3-dicarbanonaborane(13), and salts of metallic carborane anions such as bis[tri(n-butyl) ammonium]bis(undecahydrido-7-carbaundecaborate) nickelate(IV).

The ionizing ionic compounds mentioned above can be used singly or in combination of two or more kinds.

Olefin used for Polymerization

Examples of the olefins which can be polymerized by the use of the olefin polymerization solid catalyst or the prepolymerized catalyst include straight-chain or branched α-olefins of 2 to 20 carbon atoms, such as ethylene, propylene, 1-butene, 1-hexene, 4-methyl-1-pentene, 1-octene, 1-decene, 1-dodecene, 1-tetradecene, 1-hexadecene, 1-octadecene and 1-eicosene; and cycloolefins of 3 to 20 carbon atoms, such as cyclopentene, cycloheptene, norbornene, 5-methyl-2-norbornene, tetracyclododecene and 2-methyl-1,4,5,8-dimethano-1,2,3,4,4a,5, 8,8a-octahydronaphthalene. Also employable are styrene, vinylcyclohexane and dienes.

Example of dienes include chain non-conjugated dienes, such as 1,4-hexadiene, 1,6-octadiene, 2-methyl-1,5-hexadiene, 6-methyl-1,5-heptadiene and 7-methyl-1,6-octadiene; cyclic non-conjugated dienes, such as cyclohexadiene, dicyclopentadiene, methyltetrahydroindene, 5-vinylnorbornene, 5-ethylidene-2-norbornene, 5-methylene-2-norbornene, 5-isopropylidene-2-norbornene and 6-chloromethyl-5-isopropenyl-2-norbornene; 2,3-diisopropylidene-5-norbornene; 2-ethylidene-3-isopropylidene-5-norbornene; and 2-propenyl-2,2-norbornadiene.

Of these, single use of ethylene or use of ethylene and an α-olefin of 3 to 10 carbon atoms in combination is preferable.

Type of Polymerization

In the polymerization process using the olefin polymerization solid catalyst or the prepolymerized catalyst, the polymerization of an olefin is carried out usually in a gas phase or in a slurry state. In case of the slurry polymerization, an inert hydrocarbon may be used as a medium or the olefin itself may be used as a medium. Examples of the hydrocarbon media include aliphatic hydrocarbons, such as butane, isobutane, pentane, hexane, octane, decane, dodecane, hexadecane and octadecane; alicyclic hydrocarbons, such as cyclopentane, methylcyclopentane, cyclohexane and cyclooctane; and petroleum fractions, such as kerosine and gas oil.

It is preferable that the polymerization of an olefin using the olefin polymerization solid catalyst or the prepolymerized catalyst is carried out in a gas phase, and it is particularly preferable that the polymerization of an olefin using the prepolymerized catalyst is carried out in a gas phase.

Polymerization Conditions

In the slurry polymerization of an olefin using the olefin polymerization solid catalyst or the prepolymerized catalyst, the polymerization temperature is in the range of usually −50 to 120° C., preferably 0 to 100° C.

In the gas phase polymerization of an olefin using the olefin polymerization solid catalyst or the prepolymerized catalyst, the polymerization temperature is in the range of usually 0 to 120° C., preferably 20 to 100° C.

The polymerization pressure is in the range of usually atmospheric pressure to 100 kg/cm$^2$, preferably 2 to 50 kg/cm$^2$. The polymerization can be carried out by any of batchwise, semi-continuous and continuous processes. Further, the polymerization can be conducted in two or more stages under different reaction conditions.

The polymerization may be carried out in the presence of a molecular weight modifier such as hydrogen.

In the slurry polymerization or the gas phase polymerization using the olefin polymerization solid catalyst or the prepolymerized catalyst, the metallocene catalyst component is used in such an amount that the concentration of the transition metal atom in the polymerization reaction system becomes usually $10^{-8}$ to $10^{-2}$ g·atom/l, preferably $10^{-7}$ to $10^{-3}$ g·atom/l. The ratio of the transition metal (M) in the metallocene catalyst component to the aluminum atom (Al) in the solid aluminoxane (M/Al) is in the range of usually 0.0001 to 0.2, preferably 0.0005 to 0.05, more preferably 0.001 to 0.02. If the ratio is higher than 0.2, the polymerization activity of the catalyst may be lowered. If the ratio is lower than 0.0001, the polymerization activity based on the aluminum atom may be lowered.

The olefin polymerization solid catalyst or the prepolymerized catalyst according to the invention has a high void. Therefore, diffusion of a monomer can be promoted to inhibit distribution of monomer concentration, and a uniform olefin polymer having a narrow molecular weight distribution and a narrow composition distribution can be produced.

Olefin Polymer

When an olefin is polymerized in the above-described manner, a novel olefin polymer having the following properties can be obtained. The olefin polymer has an average particle diameter of usually 100 to 100,000 μm, particularly 200 to 50,000 μm, and a bulk density of usually 0.05 to 0.55 g/cc.

Process for Preparing Prepolymerized Catalyst for Olefin Polymerization

The process for preparing a prepolymerized catalyst for olefin polymerization according to the invention is described below.

The process for preparing a prepolymerized catalyst for olefin polymerization according to the invention comprises prepolymerizing an olefin in the presence of the aforesaid metallocene catalyst component, a specific aluminoxane, and optionally, an organoaluminum compound.

The aluminoxane for use in the invention is an aluminoxane which is precipitated in the prepolymerization stage in an amount of not less than 80% by weight, preferably not less than 95% by weight, based on the whole amount of the aluminoxane present in the system or an aluminoxane which has been already precipitated and is solid. This aluminoxane is referred to as "precipitatable aluminoxane" hereinafter.

The precipitatable aluminoxane may be the aforesaid solid aluminoxane or may be an aluminoxane which is precipitated in an amount of not less than 80% by weight based on the whole amount of the aluminoxane dissolved in the prepolymerization medium under the prepolymerization conditions.

In the process for preparing a prepolymerized catalyst for olefin polymerization according to the invention, an olefin is prepolymerized in the presence of the metallocene catalyst component, the precipitatable aluminoxane, and if necessary, an organoaluminum compound. In this process, it is preferable that a solid catalyst wherein the metallocene catalyst component is supported on the precipitatable aluminoxane is first formed and then an olefin is prepolymerized in the presence of the solid catalyst and if necessary the organoaluminum compound.

In the process for preparing a prepolymerized catalyst for olefin polymerization using the precipitatable aluminoxane, the same procedure and the same conditions as in the aforesaid process for preparing an olefin polymerization catalyst using the solid aluminoxane are adopted, except that the prepolymerization is conducted at an olefin partial pressure of not more than 4 $kg/cm^2$-G, preferably not more than 3.8 $kg/cm^2$-G, in a liquid phase, to form a solid catalyst and to carry out prepolymerization.

If the olefin partial pressure in the prepolymerization exceeds 4 $kg/cm^2$-G, prepolymerized catalyst particles sometimes adhere to each other or to the polymerization reactor wall in the prepolymerization stage.

The resulting solid catalyst has a bulk density of 0.01 to 1.0 g/cc, preferably 0.02 to 0.5 g/cc, more preferably 0.02 to 0.45 g/cc, particularly preferably 0.02 to 0.43 g/c.

The solid catalyst has an average particle diameter of 50 to 50,000 $\mu$m, preferably 200 to 10,000 $\mu$m, more preferably 500 to 5,000 $\mu$m.

In the obtained prepolymerized catalyst for olefin polymerization, the $\alpha$-olefin is desirably polymerized in an amount of 1 to 50,000 g, preferably 10 to 20,000 g, more preferably 100 to 15,000 g, based on 1 mg·atom of the metallocene catalyst component in the solid catalyst. The prepolymerized catalyst desirably has an average particle diameter of 50 to 80,000 $\mu$m, preferably 500 to 5,000 $\mu$m, and has a bulk density of preferably 0.01 to 0.2 g/cc.

The prepolymerized catalyst for olefin polymerization obtained by the process of the invention exhibits extremely high activity even when applied to olefin polymerization using any of a suspension polymerization process and a gas phase polymerization process. Especially in the gas phase polymerization process, the prepolymerized catalyst exhibits high activity, and a uniform polymer can be obtained. Also, a polymer containing a large amount of a rubber in the range of elastomer can be obtained. It is highly important that the polymer in the range of elastomer can be efficiently obtained even in a gas phase or in a slurry state though this has been hitherto difficult.

Polymerization of Olefin

Examples of the olefins which can be polymerized by the use of the prepolymerized catalyst for olefin polymerization obtained by the process of the invention include the same straight-chain or branched $\alpha$-olefins and cycloolefins as previously described. Also employable are styrene, vinylcyclohexane and the same dienes as previously described.

Of these, single use of ethylene or use of ethylene and an $\alpha$-olefin of 3 to 10 carbon atoms in combination is preferable.

In the polymerization process using the prepolymerized catalyst for olefin polymerization, the polymerization of an olefin is carried out usually in a gas phase or in a slurry state. In case of the slurry polymerization, an inert hydrocarbon may be used as a medium or the olefin itself may be used as a medium.

In the slurry polymerization or the gas phase polymerization of an olefin using the prepolymerized catalyst for olefin polymerization, the same polymerization temperature and the same polymerization pressure as in the aforesaid slurry polymerization or gas phase polymerization of an olefin using the olefin polymerization catalyst or the prepolymerized catalyst can be adopted. The polymerization can be carried out by any of batchwise, semi-continuous and continuous processes. Further, the polymerization can be conducted in two or more stages under different reaction conditions. The polymerization may be carried out in the presence of a molecular weight modifier such as hydrogen.

In the slurry polymerization or the gas phase polymerization of an olefin using the prepolymerized catalyst for olefin polymerization, the metallocene catalyst component and the precipitatable aluminoxane are used in the same amounts as in the aforesaid slurry polymerization or gas phase polymerization of an olefin using the olefin polymerization catalyst or the prepolymerized catalyst.

The prepolymerized catalyst for olefin polymerization obtained by the process of the invention has a high void. Therefore, diffusion of a monomer can be promoted to inhibit distribution of monomer concentration, and a uniform olefin polymer having a narrow molecular weight distribution and a narrow composition distribution can be produced. The olefin polymer has an average particle diameter of usually 100 to 100,000 $\mu$m, particularly 200 to 50,000 $\mu$m, and a bulk density of usually 0.005 to 0.55 g/cc.

Solid Olefin Polymerization Catalyst Component

The solid olefin polymerization catalyst component according to the invention is described below. The term "catalyst component" used herein means both of a component having an ability of polymerizing an olefin when used singly and a component having no ability of polymerizing an olefin when used singly.

The solid olefin polymerization catalyst component of the invention has an average particle diameter of 50 to 80,000 $\mu$m, preferably 500 to 5,000 $\mu$m, and a bulk density of 0.01 to 0.2 g/cc, preferably 0.03 to 0.1 g/cc, and substantially consists of a polyolefin and an aluminoxane.

The total content of the polyolefin and the aluminoxane in the solid olefin polymerization catalyst component of the invention is in the range of 90 to almost 100%, preferably not less than 95% and less than 100%. The content of the polyolefin is in the range of 90 to 99.999%, preferably 98 to 99.99%, and the content of the aluminoxane is in the range of 0.0001 to 0.05%, preferably 0.005 to 0.01%.

It is preferable that the solid olefin polymerization catalyst component of the invention contains no inorganic carrier.

The solid olefin polymerization catalyst component of the invention is preferably a prepolymerized catalyst component obtained by prepolymerizing an olefin in the presence of the following aluminoxane and the aforesaid metallocene catalyst component.

Aluminoxane

The aluminoxane for use in the invention is an aluminoxane selected from the group consisting of an aluminoxane represented by the aforesaid formula (I), an aluminoxane represented by the aforesaid formula (II) and an aluminoxane having a recurring unit represented by the aforesaid formula (IIIa) and a recurring unit represented by the aforesaid formula (IIIb).

There is no specific limitation on the properties of the aluminoxane for use in the invention, but the aluminoxane is preferably a solid aluminoxane having the properties previously described.

Process for Preparing Prepolymerized Catalyst Component

The prepolymerized catalyst component can be prepared by prepolymerizing an olefin in the presence of the metallocene catalyst component, the aluminoxane (preferably solid aluminoxane), and optionally, an organoaluminum compound. In this case, it is preferable that a solid catalyst wherein the metallocene catalyst component is supported on the aluminoxane is first formed and then an olefin is prepolymerized in the presence of the solid catalyst and if necessary the organoaluminum compound.

In the preparation of the prepolymerized catalyst component using the aluminoxane, the same procedure and the same conditions as in the aforesaid process for preparing an olefin polymerization catalyst using the solid aluminoxane are adopted to form a solid catalyst and to carry out prepolymerization.

The bulk density of the resulting solid catalyst is in the range of 0.01 to 1.0 g/cc, preferably 0.02 to 0.5 g/cc, more preferably 0.02 to 0.45 g/cc, particularly preferably 0.02 to 0.43 g/c. The aluminum volume concentration in n-hexane is in the range of usually 0.02 to 1.0 mmol/cc, preferably 0.04 to 0.5 mmol/cc, particularly preferably 0.05 to 0.2 mmol/cc.

The solid catalyst has an average particle diameter of 50 to 50,000 $\mu$m, preferably 200 to 10,000 $\mu$m, more preferably 500 to 5,000 $\mu$m.

In the prepolymerized catalyst component, the $\alpha$-olefin is desirably polymerized in an amount of 1 to 50,000 g, preferably 10 to 20,000 g, more preferably 100 to 15,000 g, based on 1 mg·atom of the metallocene catalyst component in the solid catalyst. The average particle diameter of the prepolymerized catalyst component is in the range of preferably 500 to 5,000 $\mu$m, and the bulk density thereof is in the range of preferably 0.01 to 0.2 g/cc.

The prepolymerized catalyst component obtained by the above process exhibits extremely high activity even when applied to olefin polymerization using any of a suspension polymerization process and a gas phase polymerization process. Especially in the gas phase polymerization process, the prepolymerized catalyst component exhibits high activity, and a uniform polymer can be obtained. Also, a polymer containing a large amount of a rubber in the range of elastomer can be obtained. It is highly important that the polymer in the range of elastomer can be efficiently obtained even in a gas phase or in a slurry state though this has been hitherto difficult.

Polymerization of Olefin

If the solid olefin polymerization catalyst component of the invention has no ability of polymerizing an olefin when used singly, it is used in combination with the aforesaid metallocene catalyst component.

Examples of the olefins which can be polymerized by the use of the solid olefin polymerization catalyst component of the invention include the same straight-chain or branched $\alpha$-olefins and cycloolefins as previously described. Also employable are styrene, vinylcyclohexane and the same dienes as previously described.

Of these, single use of ethylene or use of ethylene and an $\alpha$-olefin of 3 to 10 carbon atoms in combination is preferable.

In the polymerization process using the solid olefin polymerization catalyst component, the polymerization of an olefin is carried out usually in a gas phase or in a slurry state. In case of the slurry polymerization, the inert hydrocarbon as mentioned above may be used as a medium or the olefin itself may be used as a medium.

In the slurry polymerization or the gas phase polymerization of an olefin using the solid olefin polymerization catalyst component, the same polymerization temperature and the same polymerization pressure as in the aforesaid slurry polymerization or gas phase polymerization of an olefin using the olefin polymerization catalyst or the prepolymerized catalyst can be adopted. The polymerization can be carried out by any of batchwise, semi-continuous and continuous processes. Further, the polymerization can be conducted in two or more stages under different reaction conditions. The polymerization may be carried out in the presence of a molecular weight modifier such as hydrogen.

In the slurry polymerization or the gas phase polymerization of an olefin using the solid olefin polymerization catalyst component, the metallocene catalyst component and the solid aluminoxane are used in the same amounts as in the aforesaid slurry polymerization or gas phase polymerization of an olefin using the olefin polymerization catalyst or the prepolymerized catalyst.

The solid olefin polymerization catalyst component of the invention has a high void. Therefore, diffusion of a monomer can be promoted to inhibit distribution of monomer concentration, and a uniform olefin polymer having a narrow molecular weight distribution and a narrow composition distribution can be produced.

The olefin polymer has an average particle diameter of usually 100 to 100,000 $\mu$m, particularly 200 to 50,000 $\mu$m, and a bulk density of usually 0.05 to 0.55 g/cc.

EFFECT OF THE INVENTION

When the solid aluminoxane of the invention is used, a porous olefin polymerization catalyst is obtained. When this catalyst is used to polymerize an olefin, porous polymer particles are obtained. Because of high bulk density, the thus obtained polymer particles retain a large amount of gas, and therefore they can be used, as they are, for sound insulating materials or heat insulating materials which need high sound insulating effects or high heat insulating effects.

By the use of the solid aluminoxane of the invention as an olefin polymerization catalyst component, the activity of the catalyst can be increased and polymers or copolymers having narrow composition distribution can be produced. By the use of the solid aluminoxane as an olef in polymerization catalyst component, further, a catalyst capable of containing a large amount of a rubber in the range of elastomer can be prepared though such a catalyst has been hardly obtained hitherto, and therefore an olefin polymer containing a large amount of a rubber in the range of elastomer can be efficiently produced. Especially in the gas phase polymerization, an olefin polymer in the range of elastomer can be produced stably and efficiently. Accordingly, occurrence of powder agglomerates and occurrence of a string polymer, which are problems in the random copolymerization stage in the conventional process for preparing a propylene block copolymer, can be inhibited, and thereby polymerization can be stably carried out for a long period of time.

The polymer particles obtained by the gas phase polymerization can be used, as they are, after they are taken out of the polymerization reactor, because it is unnecessary to remove volatiles such as a solvent from the polymer particles.

In the process for preparing a prepolymerized catalyst for olefin polymerization according to the invention, prepolymerized catalyst particles hardly adhere to each other or to the polymerization reactor wall in the prepolymerization stage.

Use of the solid olefin polymerization catalyst component of the invention makes it possible to increase activity of the catalyst and to produce polymers and copolymers having narrow composition distribution. The solid olefin polymerization catalyst component of the invention can contain a large amount of a rubber in the range of elastomer though the conventional ones are difficult to contain a large amount of the rubber, and therefore an olefin polymer containing a large amount of a rubber in the range of elastomer can be efficiently produced. Especially in the gas phase polymerization, an olefin polymer in the range of elastomer can be produced stably and efficiently. Accordingly, occurrence of powder agglomerates and occurrence of a string polymer, which are problems in the random copolymerization stage in the conventional process for preparing a propylene block copolymer, can be inhibited, and thereby polymerization can be stably carried out for a long period of time.

EXAMPLE

The present invention is further described with reference to the following examples, but it should be construed that the invention is in no way limited to those examples.

Example 1

Preparation of Solid Aluminoxane

Using PMAO (polymethylaluminoxane) available from Witco Co., a solid aluminoxane was prepared. The aluminoxane used herein contained alkyl groups consisting of methyl groups only and had an alkyl group/aluminum atom ratio of 1.8. The alkyl group/aluminum atom ratio was determined in the following manner.

To a 100-ml glass container equipped with a stirrer, 2 mmol (in terms of aluminum atom) of an aluminoxane solution (aluminum atom concentration: 0.06 mmol/ml) was introduced at room temperature in the blanketed state with nitrogen. Then, 10 ml of a 0.5 N sulfuric acid aqueous solution was dropwise added over a period of 10 to 15 minutes to carry out hydrolysis. The gas generated in the hydrolysis was replaced with water to capture the gas in a burette. Then, the volume of the gas was measured, and also the composition of the gas was determined by gas chromatography. Further, the volume of the liquid after the hydrolysis was measured, and also the composition of the liquid was determined by gas chromatography. From the results, the amount of methane contained in the gas and in the liquid was calculated. The ratio of the methane to the aluminum atom was taken as the ratio of the alkyl group to the aluminum atom (alkyl group/aluminum atom ratio). The molecular weight, as determined by freezing point depression in benzene, was 876. Therefore, the degree of polymerization of the aluminoxane was 15. This methylaluminoxane was soluble in toluene at 25° C. in an aluminum atom concentration of up to 1.5 mol/l. The dissolution proportion of the methylaluminoxane in n-hexane at 25° C. was 0.8% by mol.

To a 300-ml pressure-reducible reactor equipped with a stirrer, 150 ml of purified n-hexane was introduced at room temperature with stirring. To the n-hexane, 30 ml of a toluene solution of the aluminoxane, which had been adjusted to a concentration of 1.0 ml/l, was introduced in the whole amount within 5 seconds at room temperature with stirring. The dissolution proportion of the aluminoxane in the mixed solvent of n-hexane and toluene was 1.8% by mol. The aluminoxane introduced was instantaneously (within 1 second) precipitated up to the equilibrium dissolution proportion. Then, the temperature of the reactor was raised to 35° C. over a period of about 3 hours with reducing the pressure in the reactor to 4 Torr by means of a vacuum pump, whereby the solvent in the reactor was removed to further precipitate the methylaluminoxane. The reaction liquid was filtered through a filter to remove a liquid phase portion and to obtain a solid aluminoxane. The solid aluminoxane had an average particle diameter of 210 $\mu$m and a bulk density of 0.42 g/cc. The aluminum volume concentration in n-hexane was 0.15 mmol/ml.

The aluminum volume concentration in n-hexane was determined in the following manner. A 100-ml gas-replaceable measuring cylinder was purged with nitrogen, and to the cylinder was introduced 50 cc of a n-hexane slurry of the above-obtained aluminoxane (concentration: 0.02 mmol/ml). Thereafter, the measuring cylinder was allowed to stand for 24 hours or more, and the interface between the sediment (sedimented slurry) and the supernatant was visually observed, followed by measuring volume of the sedimented slurry. The amount (1 mmol) of the aluminoxane introduced was divided by the volume of the sedimented slurry, and the obtained value was taken as the aluminum volume concentration in n-hexane.

Example 2

2 Preparation of Solid Aluminoxane

Using an aluminoxane (MMAO–3A) available from Tohso Aquezo Co., a solid aluminoxane was prepared. The aluminoxane used herein contained alkyl groups consisting of methyl groups and i-butyl groups (methyl/i-butyl=7/3) and had an alkyl group/aluminum atom ratio of 1.6. The alkyl group/aluminum atom ratio was determined in the same manner as in Example 1. The analyses of the gas and the liquid were made to calculate the amounts of both of methane and i-butane. The ratio of the total of the methane and the i-butane to the aluminum atom was taken as the ratio of the alkyl group to the aluminum atom (alkyl group/aluminum atom ratio). The molecular weight, as determined by freezing point depression in benzene, was 952. Therefore, the degree of polymerization of the aluminoxane was 13. This aluminoxane was soluble in toluene at 25° C. and n-hexane in an aluminum atom concentration of up to 1.5 mol/l.

To a 300-ml pressure-reducible reactor equipped with a stirrer, 150 ml of an aluminoxane solution which had been adjusted to a concentration of 0.2 mol/l by using a purified n-hexane was introduced. Separately, nitrogen was bubbled in water to adjust the water concentration in nitrogen to 0.018 g/N—l—$N_2$, and the nitrogen was then bubbled in the aluminoxane solution at a rate of 2 N—l/hr for 6 hours. After the introduction of nitrogen, the aluminoxane was precipitated with time. The alkyl group/aluminum atom ratio after the reaction with water was 1.2. Then, the solvent was removed by the same operation as in Example 1 to obtain a solid aluminoxane. The solid aluminoxane had an average particle diameter of 350 μm and a bulk density of 0.39 g/cc. The aluminum volume concentration in n-hexane was 0.12 mmol/ml.

Example 3

Prepolymerization

To a 2-liter reactor equipped with a stirrer, 0.5 liter of dehydrated and purified n-hexane was introduced in a nitrogen atmosphere. Then, 2.9 mmol (in terms of aluminum atom) of the aluminoxane slurry given before the solvent removal operation in Example 2, 4.9 mmol of triisobutylaluminum and 0.0049 mmol of bis(1,3-dimethylcyclopentadienyl)zirconium dichloride were fed, and purified n-hexane was added so that the whole amount of the solvent became 1 liter.

Then, nitrogen was purged out of the reactor with ethylene, and prepolymerization was carried out for 1 hour at room temperature under the total pressure of 4.0 kg/cm$^2$ (3.0 kg/cm$^2$-G). After the reactor was purged with nitrogen, the resulting prepolymerized catalyst slurry was taken out of the reactor and separated into a solvent and a prepolymerized catalyst by a glass filter. The prepolymerized catalyst was subjected to decantation 4 times with 20 ml of hexane per 1 g of the prepolymerized catalyst, and then dried over heated nitrogen to obtain 11 g of a prepolymerized catalyst. The prepolymerized catalyst had an average particle diameter of 800 μm and a bulk density of 0.05 g/cc.

Example 4

Polymerization

To a 2-liter autoclave equipped with a stirrer and purged with nitrogen, 100 g of sufficiently dehydrated salt was introduced. Then, the temperature of the autoclave was raised to 70° C., and the autoclave was purged with ethylene. Thereafter, 10 g of the prepolymerized catalyst obtained in Example 3 was fed, and a mixed gas of ethylene and propylene (ethylene/propylene=1/1, by mol) was further fed at a rate of 300 N-1/hr to perform polymerization for 1 hour, while removing the gas so that the pressure became 9 kg/cm$^2$ (8 kg/cm$^2$-G). The polymerization was able to be stably carried out without adhesion of a polymer to the reactor wall surface. After the polymerization was completed, the solid was collected, washed with a large amount of water to remove the salt and dried to obtain 32.3 g of a copolymer. The copolymer had an average particle diameter of 820 μm and a bulk density of 0.19 g/cc.

To 200 ml of decane, 1 g of the obtained polymer was added, and the mixture was heated to 150° C. to give a solution. The solution was cooled to 60° C. over a period of 5 hours and separated into insolubles and a decane-soluble component by filtration. As a result of recovering the decane-soluble component, the proportion of the decane-soluble component was found to be 65.3% by weight. Thus, it was found that the resulting polymer contained 21.1 g of decane-soluble ethylene/propylene copolymer. The decane-soluble component had an ethylene content of 79% by mol and an intrinsic viscosity (η), as measured in decalin at 135° C., of 1.91 dl/g.

Example 5

Preparation of Precipitatable Aluminoxane

Using MMAO (methylaluminoxane) available from Tohso Aquezo Co., a precipitatable aluminoxane carrier was prepared. The aluminoxane used herein contained alkyl groups consisting of methyl groups and isobutyl groups (methyl/isobutyl=7/3) and had an alkyl group/aluminum atom ratio of 1.69. The alkyl group/aluminum atom ratio was determined in the following manner.

To a 100-ml glass reactor equipped with a stirrer, 33.33 ml of hexane and 2 mmol (in terms of aluminum atom) of an aluminoxane solution were introduced at room temperature in the blanketed state with nitrogen so that the aluminum atom concentration became 0.06 mmol/ml. Then, 10 ml of a 0.5 N sulfuric acid aqueous solution was dropwise added over a period of 10 minutes to carry out hydrolysis. The gas generated in the hydrolysis was replaced with water to capture the gas in a burette. Then, the volume of the gas was measured, and also the composition of the gas was determined by gas chromatography. Further, the volume of the liquid after the hydrolysis was measured, and also the composition of the liquid was determined by gas chromatography. From the results, the amount of methane and the amount of isobutane contained in the gas and in the liquid were calculated. The ratio of the total of the methane and the isobutane to the aluminum atom was taken as the ratio of the alkyl group to the aluminum atom (alkyl group/aluminum atom ratio).

To a 500-ml glass reactor equipped with a stirrer, dehydrated and purified n-hexane and an aluminoxane solution were introduced in the total amount of 250 ml with stirring at room temperature in the blanketed state with nitrogen so that the aluminum atom concentration became 0.2 mmol/ml. Separately, nitrogen was bubbled in water to adjust the water concentration in nitrogen to 20.5 mg/N—l—$N_2$, and the nitrogen was then bubbled in the aluminoxane solution at a rate of 2.4 l/hr for 5.5 hours. The aluminoxane was precipitated with time. The alkyl group/aluminum atom ratio after the reaction with water was 1.11. Then, the temperature of the reactor was raised to 35° C. over a period of about 3 hours with reducing the pressure in the reactor to 4 Torr by means of a vacuum pump, whereby the solvent in the reactor was removed to further precipitate the methylaluminoxane. The reaction liquid was filtered through a filter to remove a liquid phase portion and to obtain a solid aluminoxane carrier. The solid aluminoxane carrier had an average particle diameter of 350 μm and a bulk density of 0.29 g/cc. The aluminum volume concentration in n-hexane was 0.11 mmol/ml.

Preolymerization

To a 2-liter reactor equipped with a stirrer, 0.5 liter of dehydrated and purified n-hexane was introduced in a nitrogen atmosphere. Then, 1.2 mmol (in terms of aluminum atom) of the aluminoxane slurry given before the solvent removal operation in the above step "Preparation of precipitatable aluminoxane", 1.0 mmol of triisobutylaluminum and 0.002 mmol of bis(1,3-dimethylcyclopentadienyl)zirconium dichloride were fed, and purified n-hexane was added so that the whole amount of the solvent became 1 liter.

Then, nitrogen was purged out of the reactor with ethylene, and prepolymerization was carried out for 1 hour at 50° C. under the total pressure of 4.0 kg/cm² (3 kg/cm²-G, ethylene partial pressure: 3.4 kg/cm²). After the reactor was purged with nitrogen, the resulting prepolymerization slurry was taken out of the reactor and separated into a solvent and a prepolymerized catalyst by a glass filter. The prepolymerized catalyst was subjected to decantation 4 times with 20 ml of n-hexane per 1 g of the prepolymerized catalyst, and then dried over nitrogen heated at 50° C. to obtain 21 g of a prepolymerized catalyst. The prepolymerized catalyst had an average particle diameter of 2.2 mm and a bulk density of 0.05 g/cc. After the prepolymerization, the inside of the reactor was inspected, and as a result, adhesion of a polymer to the reactor wall surface was not observed.

Reference Experiment

The procedure of Example 5 was repeated except that the total pressure in the prepolymerization was varied to 6.0 kg/cm² (5 kg/cm²-G, ethylene partial pressure: 5.4 kg/cm²) from 4.0 kg/cm² (3 kg/cm²-G, ethylene partial pressure: 3.4 kg/cm²).

As a result, 36 g of a prepolymerized catalyst was obtained. A part of the prepolymerized catalyst particles were agglomerated, and when the inside of the reactor was inspected after the prepolymerization, adhesion of a polymer to the reactor wall surface was observed.

Example 6

Preparation of Precipitatable Aluminoxane

Using MMAO (methylaluminoxane) available from Tohso Aquezo Co., a precipitatable aluminoxane carrier was prepared. The aluminoxane used herein contained alkyl groups consisting of methyl groups and isobutyl groups (methyl/isobutyl=7/3) and had an alkyl group/aluminum atom ratio of 1.69. The alkyl group/aluminum atom ratio was measured in the same manner as previously described.

To a 500-ml glass reactor equipped with a stirrer, dehydrated and purified n-hexane and an aluminoxane solution were introduced in the total amount of 250 ml with stirring at room temperature in the blanketed state with nitrogen so that the aluminum atom concentration became 0.2 mmol/ml. Separately, nitrogen was bubbled in water to adjust the water concentration in nitrogen to 20.5 mg/N—1—N₂, and the nitrogen was then bubbled in the aluminoxane solution at a rate of 2.4 l/hr for 5.5 hours. The aluminoxane was precipitated with time. The alkyl group/aluminum atom ratio after the reaction with water was 1.11. Then, the temperature of the reactor was raised to 35° C. over a period of about 3 hours with reducing the pressure in the reactor to 4 Torr by means of a vacuum pump, whereby the solvent in the reactor was removed to further precipitate the methylaluminoxane. The reaction liquid was filtered through a filter to remove a liquid phase portion and to obtain a precipitatable aluminoxane. The precipitatable aluminoxane had an average particle diameter of 350 μm and a bulk density of 0.29 g/cc. The aluminum volume concentration in n-hexane was 0.11 mmol/ml.

Prepolymerization

To a 2-liter reactor equipped with a stirrer, 0.5 liter of dehydrated and purified n-hexane was introduced in a nitrogen atmosphere. Then, 2.4 mmol (in terms of aluminum atom) of the aluminoxane slurry given before the solvent removal operation in the above step "Preparation of precipitatable aluminoxane", 2.0 mmol of triisobutylaluminum and 0.004 mmol of bis(1,3-dimethylcyclopentadienyl)zirconium dichloride were fed, and purified n-hexane was added so that the whole amount of the solvent became 1 liter.

Then, nitrogen was purged out of the reactor with ethylene, and prepolymerization was carried out for 1 hour at 50° C. under the total pressure of 4.0 kg/cm² (3.0 kg/cm²-G). After the reactor was purged with nitrogen, the resulting prepolymerization slurry was taken out of the reactor and separated into a solvent and a prepolymerized catalyst by a glass filter. The prepolymerized catalyst was subjected to decantation 4 times with 20 ml of n-hexane per 1 g of the prepolymerized catalyst, and then dried over nitrogen heated at 50° C. to obtain 40 g of a prepolymerized catalyst. The prepolymerized catalyst had an average particle diameter of 2.5 mm and a bulk density of 0.052 g/cc. After the prepolymerization, the inside of the reactor was inspected, and as a result, adhesion of a polymer to the reactor wall surface was not observed.

Polymerization

To a 1.7-liter autoclave equipped with a stirrer and purged with nitrogen, 250 g of sufficiently dehydrated salt was introduced. Then, the temperature of the autoclave was raised to 80° C., and the autoclave was purged with ethylene. Thereafter, 10 g of the prepolymerized catalyst obtained in the above step "Prepolymerization" was fed, and a mixed gas of ethylene and propylene (ethylene/propylene=1/1, by mol) was further fed at the lower part of the autoclave at a rate of 300 N-1/hr to perform polymerization for 1 hour, while removing the gas so that the pressure became 9 kg/cm² (8 kg/cm²-G). The polymerization was able to be stably carried out without adhesion of a polymer to the reactor wall surface. After the polymerization was completed, the solid was collected, washed with a large amount of water to remove the salt and dried to obtain 24 g of a polymer. The polymer had an average particle diameter of 2.8 mm and a bulk density of 0.11 g/cc.

To 200 ml of decane, 1 g of the obtained polymer was added, and the mixture was heated to 150° C. to give a solution. The solution was cooled to 90° C. over a period of 2 hours and separated into insolubles and a decane-soluble component by filtration. As a result of recovering the decane-soluble component, the proportion of the decane-soluble component was found to be 55%, and 0.55 g of an ethylene/propylene copolymer was obtained. The decane-soluble component had an ethylene content of 82% by mol and an intrinsic viscosity (η), as measured in decalin at 135° C., of 2.2 dl/g.

Then, 2 g of the polymer was introduced into 100 cc of methyl acetate at 50° C. After stirring for 1 hour, the mixture was separated into a solution and insolubles by filtration. The solution was dried to measure weight of the soluble component, and as a result it was 0.004 g. The dissolution proportion in methyl acetate, that is an indication of a composition distribution, was approx. 0.2%, and the composition distribution was confirmed to be sufficiently narrow.

What is claimed is:

1. A solid aluminoxane useful for catalyst carrier, said aluminoxane having an average particle diameter of 210 to 10,000 μm, and which is selected from the group consisting of an aluminoxane represented by the following formula (I), an aluminoxane represented by the following formula (II) and an aluminoxane having a recurring unit represented by the following formula (IIIa) and a recurring unit represented by the following formula (IIIb) and has a bulk density of 0.01 to 1.0 g/cc;

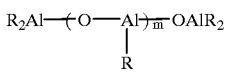  (I)

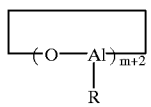  (II)

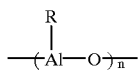  (IIIa)

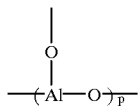  (IIIb)

wherein R is a hydrocarbon group of 1 to 10 carbon atoms, m is an integer of 2 to 500, and n and p are each an integer of 1 or more.

2. A process for preparing a solid aluminoxane useful for catalyst carrier, comprising bringing a solution of an aluminoxane which is selected from the group consisting of an aluminoxane represented by the following formula (I), an aluminoxane represented by the following formula (II) and an aluminoxane having a recurring unit represented by the following formula (IIIa) and a recurring unit represented by the following formula (IIIb), and which has a bulk density of 0.01 to 1.0 g/cc;

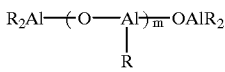  (I)

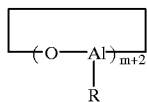  (II)

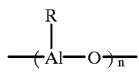  (IIIa)

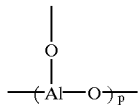  (IIIb)

wherein R is a hydrocarbon group of 1 to 10 carbon atoms, m is an integer of 2 to 500, and n and p are each an integer of 1 or more and having an alkyl group/aluminum atom ratio of not less than 1.5 into contact with a solvent insolubilizing or slightly solubilizing the aluminoxane to precipitate the aluminoxane in such a manner that at least 80% by weight based on the total amount of the aluminoxane to be precipitated is precipitated within 60 seconds from the beginning of precipitation.

3. A process for preparing a solid aluminoxane useful for catalyst carrier, comprising causing a solution of an aluminoxane which is selected from the group consisting of an aluminoxane represented by the following formula (I), an aluminoxane represented by the following formula (II) and an aluminoxane having a recurring unit represented by the following formula (IIIa) and a recurring unit represented by the following formula (IIIb), and which has a bulk density of 0.01 to 1.0 g/cc;

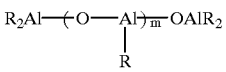  (I)

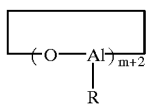  (II)

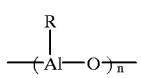  (IIIa)

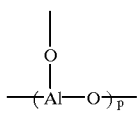  (IIIb)

wherein R is a hydrocarbon group of 1 to 10 carbon atoms, m is an integer of 2 to 500, and n and p are each an integer of 1 or more, and having an alkyl group/aluminum atom ratio of not less than 1.5 to react with water until the alkyl group/aluminum atom ratio of the aluminoxane becomes 1.0 to 1.5 to precipitate the aluminoxane.

4. An olefin polymerization catalyst comprising:
(A) a metallocene catalyst component supported on
(B) a solid aluminoxane having an average particle diameter of 210 to 10,000 μm, and which is selected from the group consisting of an aluminoxane represented by the following formula (I), an aluminoxane represented by the following formula (II) and an aluminoxane having a recurring unit represented by the following formula (IIIa) and a recurring unit represented by the following formula (IIIb) and has a bulk density of 0.01 to 1.0 g/cc;

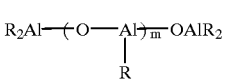  (I)

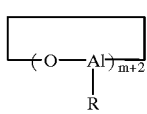  (II)

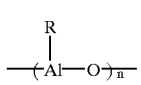  (IIIa)

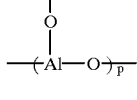
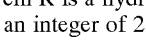  (IIIb)

wherein R is a hydrocarbon group of 1 to 10 carbon atoms, m is an integer of 2 to 500, and n and p are each an integer of 1 or more.

5. The olefin polymerization catalyst as claimed in claim 4, wherein the metallocene catalyst component (A) is a transition metal compound represented by the following formula (IV) or (V):

$$ML_x \quad (IV)$$

wherein M is a transition metal atom selected from Group 4 of the periodic table, L is a ligand coordinated to the transition metal atom, at least one ligand L is a ligand having cyclopentadienyl skeleton, L other than the ligand having cyclopentadienyl skeleton is a hydrocarbon group of 1 to 12 carbon atoms, an alkoxy group, an aryloxy group, a trialkylsilyl group, a —SO$_3$R group (R is a hydrocarbon group of 1 to 8 carbon atoms which may have a substituent such as halogen), a halogen atom or a hydrogen atom, and x is a valence of the transition metal atom;

$$L^1MX_2 \quad (V)$$

wherein M is a transition metal atom selected from Group 4 of the periodic table, L$^1$ is a derivative of a delocalized π-bond group and imparts a restraint geometric shape to the active site of the metal M, and each X is the same or different and is a hydrogen atom, a halogen atom, a hydrocarbon group having 20 or less carbon atoms, a silyl group having 20 or less silicon atoms or a germyl group having 20 or less germanium atoms.

6. A prepolymerized catalyst for olefin polymerization, which has an average particle diameter of 500 to 5,000 μm, and is obtained by prepolymerizing an olefin in the presence of:

(A) a metallocene catalyst component, (B) a solid aluminoxane which is selected from the group consisting of an aluminoxane represented by the following formula (I), an aluminoxane represented by the following formula (II) and an aluminoxane having a recurring unit represented by the following formula (IIIa) and a recurring unit represented by the following formula (IIIb) and has a bulk density of 0.01 to 1.0 g/cc; and optionally (C) an organoaluminum compound;

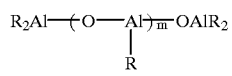

(I)

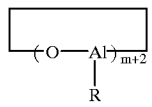

(II)

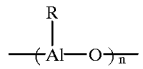

(IIIa)

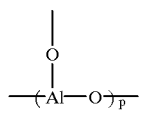

(IIIb)

wherein R is a hydrocarbon group of 1 to 10 carbon atoms, m is an imeger of 2 to 500, and n and p are each an integer of 1 or more.

7. The prepolymerized catalyst for olefin polymerization as claimed in claim 6, wherein the metallocene catalyst component (A) is a transition metal compound represented by the following formula (IV) or (V):

$$ML_x \quad (IV)$$

wherein M is a transition metal atom selected from Group 4 of the periodic table, L is a ligand coordinated to the transition metal atom, at least one ligand L is a ligand having cyclopentadienyl skeleton, L other than the ligand having cyclopentadienyl skeleton is a hydrocarbon group of 1 to 12 carbon atoms, an alkoxy group, an aryloxy group, a trialkylsilyl group, a —SO$_3$R group (R is a hydrocarbon group of 1 to 8 carbon atoms which may have a substituent such as halogen), a halogen atom or a hydrogen atom, and x is a valence of the transition metal atom;

$$L^1MX_2 \quad (V)$$

wherein M is a transition metal atom selected from Group 4 of the periodic table, L$^1$ is a derivative of a delocalized π-bond group and imparts a restraint geometric shape to the active site of the metal M, and each X is the same or different and is a hydrogen atom, a halogen atom, a hydrocarbon group having 20 or less carbon atoms, a silyl group having 20 or less silicon atoms or a germyl group having 20 or less germanium atoms.

8. The prepolymerized catalyst for olefin polymerization as claimed in claim 7, which has a bulk density of 0.01 to 0.2 g/cc.

9. A process for preparing a prepolymerized catalyst for olefin polymerization, comprising polymerizing an olefin in a liquid phase under the condition of an olefin partial pressure of not more than 4 kg/cm$^2$–G in the presence of:

(A) a metallocene catalyst component, (B) an aluminoxane having an average particle diameter of from 210 to 10,000 μm which is precipitated in the prepolymerization stage in an amount of not less than 80% by weight based on the whole amount of the aluminoxane present in the system, or an aluminoxane which has been already precipitated and is solid and which has an average particle diameter of from 210 to 10,000 μm, and optionally (C) an organoaluminum compound.

10. The process for preparing a prepolymerized catalyst for olefin polymerization as claimed in claim 9, wherein the metallocene catalyst component (A) is a transition metal compound represented by the following formula (IV) or (V):

$$ML_x \quad (IV)$$

wherein M is a transition metal atom selected from Group 4 of the periodic table, L is a ligand coordinated to the transition metal atom, at least one ligand L is a ligand having cyclopentadienyl skeleton, L other than the ligand having cyclopentadienyl skeleton is a hydrocarbon group of 1 to 12 carbon atoms, an alkoxy group, an aryloxy group, a trialkylsilyl group, a —SO$_3$R group (R is a hydrocarbon group of 1 to 8 carbon atoms which may have a substituent such as halogen), a halogen atom or a hydrogen atom, and x is a valence of the transition metal atom;

$$L^1MX_2 \quad (V)$$

wherein M is a transition metal atom selected from Group 4 of the periodic table, L$^1$ is a derivative of a delocalized π-bond group and imparts a restraint geometric shape to the active site of the metal M, and each X is the same or different and is a hydrogen atom, a halogen atom, a hydrocarbon group having 20 or less carbon atoms, a silyl group having 20 or less silicon atoms or a germyl group having 20 or less germanium atoms.

11. The process for preparing a prepolymerized catalyst for olefin polymerization as claimed in claim 9 or 10, wherein the aluminoxane (B) is a solid aluminoxane which is selected from the group consisting of an aluminoxane represented by the following formula (I), an aluminoxane represented by the following formula (II) and an aluminoxane having a recurring unit represented by the following formula (IIIa) and a recurring unit represented by the following formula (IIIb) and has a bulk density of 0.01 to 1.0 g/cc;

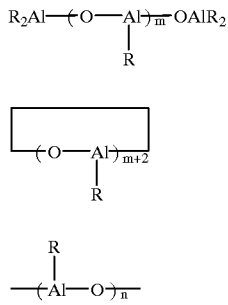

(I)

(II)

(IIIa)

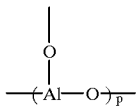

(IIIb)

wherein R is a hydrocarbon group of 1 to 10 carbon atoms, m is an integer of 2 to 500, and n and p are each an integer of 1 or more.

12. The process for preparing a prepolymerized catalyst for olefin polymerization as claimed in any one of claims 9 or 10, wherein a prepolymerized catalyst having a bulk density of 0.01 to 0.2 g/cc is prepared.

13. The process for preparing a prepolymerized catalyst for olefin polymerization as claimed in claim 11, wherein a prepolymerized catalyst having a bulk density of 0.01 to 0.2 g/cc is prepared.

* * * * *